(12) United States Patent
Kronström et al.

(10) Patent No.: US 10,779,804 B2
(45) Date of Patent: Sep. 22, 2020

(54) BIOPSY NEEDLE FOR BIOPSY SAMPLING, BIOPSY DEVICE, AND METHODS OF MANUFACTURING A BIOPSY NEEDLE OR A BIOPSY DEVICE

(71) Applicant: INJEQ OY, Tampere (FI)

(72) Inventors: Kai Kronström, Espoo (FI); Petri Ahonen, Tampere (FI); Sanna Mäki, Tampere (FI); Timo Elomaa, Pirkkala (FI); Juho Kari, Tampere (FI)

(73) Assignee: Injeq Oy, Tampere (FI)

( * ) Notice: Subject to any disclaimer, the term of this patent is extended or adjusted under 35 U.S.C. 154(b) by 327 days.

(21) Appl. No.: 15/580,118

(22) PCT Filed: Jun. 7, 2015

(86) PCT No.: PCT/IB2015/054302
§ 371 (c)(1),
(2) Date: Dec. 6, 2017

(87) PCT Pub. No.: WO2016/198910
PCT Pub. Date: Dec. 15, 2016

(65) Prior Publication Data
US 2018/0296197 A1 Oct. 18, 2018

(51) Int. Cl.
*A61B 10/02* (2006.01)
*A61B 5/053* (2006.01)
*A61B 17/00* (2006.01)

(52) U.S. Cl.
CPC ........ *A61B 10/0275* (2013.01); *A61B 5/0538* (2013.01); *A61B 10/0283* (2013.01);
(Continued)

(58) Field of Classification Search
CPC .............. A61B 10/0275; A61B 5/0538; A61B 10/0283
(Continued)

(56) References Cited

U.S. PATENT DOCUMENTS 6,337,994 B1   1/2002   Stoianovici
6,770,070 B1   8/2004   Balbierz
(Continued)

FOREIGN PATENT DOCUMENTS

EP            2783624      10/2014
WO     WO 2006119245      11/2006
(Continued)

OTHER PUBLICATIONS

International Report on Patentability in PCT Application PCT/IB2015/054302, EPO, dated Dec. 12, 2017.
(Continued)

*Primary Examiner* — Daniel L Cerioni
(74) *Attorney, Agent, or Firm* — Bourque & Associates

(57) ABSTRACT

A biopsy needle (100) comprises a cannula (5) with a distal end (15), an inner needle (1) that has a sharpened distal end (16) and at least one biopsy cavity (7) that is located at a distance (L3) from the sharpened distal end (16). The cannula (5) and the inner needle (1) are configured so that the inner needle (1) is accommodated inside the cannula (5) and the inner needle (1) and the cannula (5) are movable with regard to each other. The inner needle (1) further comprises at least two measuring electrodes (1, 4; 3, 4) for measuring a bioimpedance spectrum, the measuring electrodes (1, 4; 3, 4) defining a measuring volume that is localized to the distal end (16) of the inner needle (1).

25 Claims, 7 Drawing Sheets

(52) U.S. Cl.
CPC ........... *A61B 2010/0208* (2013.01); *A61B 2017/00026* (2013.01); *A61B 2017/00526* (2013.01)

(58) Field of Classification Search
USPC .......................................................... 600/567
See application file for complete search history.

(56) References Cited

U.S. PATENT DOCUMENTS

| | | | |
|---|---|---|---|
| 7,918,852 B2 | 4/2011 | Tullis | |
| 2002/0042594 A1 | 4/2002 | Lum | |
| 2003/0093007 A1* | 5/2003 | Wood | A61B 10/0275 600/564 |
| 2004/0010204 A1 | 1/2004 | Weber | |
| 2010/0256483 A1 | 10/2010 | Wall | |
| 2012/0123296 A1* | 5/2012 | Hashimshony | A61B 5/05 600/567 |
| 2014/0358166 A1 | 12/2014 | Kelleher et al. | |
| 2015/0038872 A1* | 2/2015 | Halter | A61B 10/0275 600/547 |

FOREIGN PATENT DOCUMENTS

| | | |
|---|---|---|
| WO | WO 2009019707 | 2/2009 |
| WO | WO 2009142918 | 11/2009 |
| WO | WO 2011016034 | 2/2011 |
| WO | WO 2009083651 | 7/2019 |

OTHER PUBLICATIONS

International Search Report and Written Opinion for PCT Application PCT/IB2015/054302, EPO, dated Feb. 3, 2016.
Communication Pursuant to Article 94(3) EPC in Application 14 722 734.2-1657, EPO, dated Oct. 27, 2017.
International Search Report in PCT Application PCT/IB2012/053333, EPO, dated Oct. 1, 2012.
Written Opinion of the International Searching Authority in PCT Application PCT/IB2012/053333, EPO.
International Preliminary Report on Patentability in PCT/IB2012/053333 dated Jun. 10, 2013.
Extended European Report in Application EP13161684.9, dated Jul. 25, 2013, EPO.
International Preliminary Report on Patentability in PCT Application, PCT/IB2014/06012, EPO, dated Sep. 9, 2015.
Written Opinion of the International Searching Authority in PCT Application PCT/IB2014/060120, EPO.
International Search Report in PCT Application PCT/IB2014/060120, EPO, dated Aug. 4, 2014.

* cited by examiner

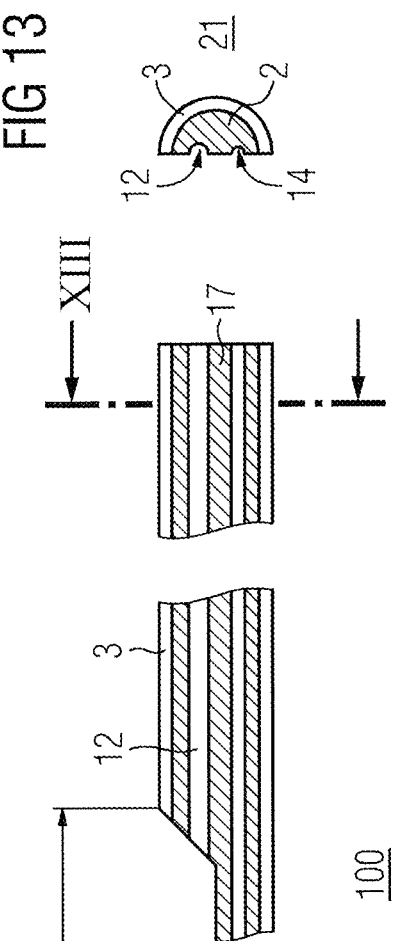
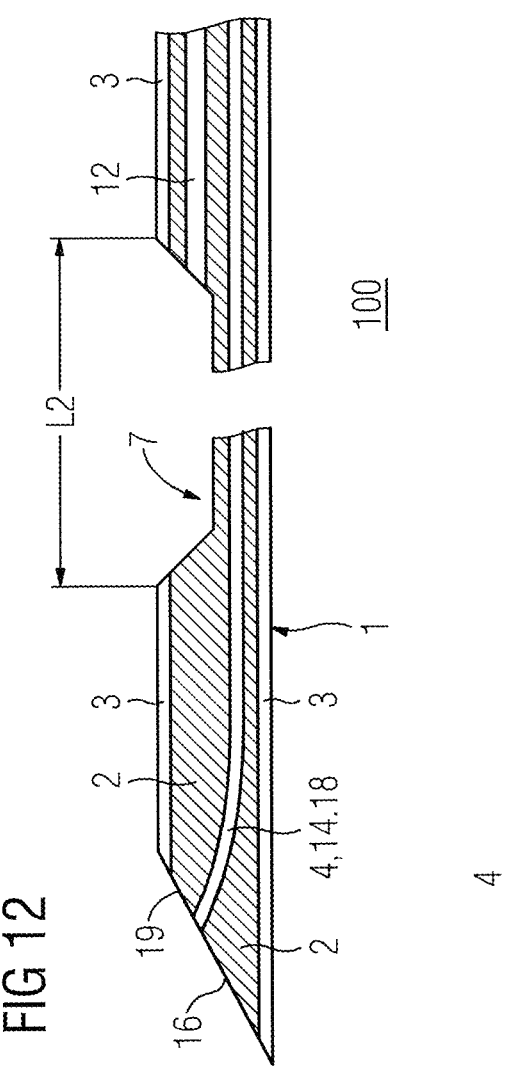

BIOPSY NEEDLE FOR BIOPSY SAMPLING, BIOPSY DEVICE, AND METHODS OF MANUFACTURING A BIOPSY NEEDLE OR A BIOPSY DEVICE

TECHNICAL FIELD

The present invention relates to medical technology, and more particularly to core needle biopsy devices and biopsy needles as well as to their manufacture.

BACKGROUND ART

Accurate diagnosis and determination of the stage of the disease are enabled by tissue samples, biopsies. They are involved in cancer detection, follow-up of treatment, estimation of disease severity and prognosis. For example, prostate biopsies are utilized for confirming suspected prostate cancer, liver biopsies for determining the progression of fibrosis and cirrhosis and response of treatment for hepatitis and renal biopsies are for different kidney diseases and dysfunctions as well as for transplantation follow-up.

Biopsies have an extremely important role since treatment decisions are often based on them. Extracted tissue sample is small in order to be minimally invasive and as a result, biopsy covers only a small portion of the total volume of the sampled organ. Because of heterogeneity and variation within the organ, the actual target may get missed. In liver tissue, for example, lesions of hepatitis are unevenly distributed which may lead to sampling error and misdiagnosis [1]. Standard prostate biopsy procedure includes several biopsies taken systematically from different sites of the organ, but is still insufficient. In fact, risk in prostate cancer for false negative detection is high: In study of Sonn et al. [2] 38% of Gleason score higher than 7 was not detected with systematic biopsy.

Electrical properties of tissues differ from each other enabling tissue discrimination by bioimpedance spectroscopy. When placing measurement electrode inside the injection needle, bioimpedance can be utilized in needle guidance [3]. The first bioimpedance probe needles were thick, but Kari et al. [4] adapted the bioimpedance measurement in bipolar fashion to a standard commercial hypodermic needle and used it with real time classifier for tissue identification.

In addition to different tissue types, cancerous and benign tissues could be differentiated: For example, malign tumors in breast, lung, prostate and kidney have shown to cause significant changes to the electrical properties of tissue [5]-[10]. Therefore the bioimpedance based targeted biopsy is expected to enable more accurate tissue sampling.

A biopsy needle is based on the same idea of a bioimpedance sensing injection needle, but it enables the tissue sample intake. A core type biopsy instrument consists of two nested needles, the outer and the inner needle with a biopsy cavity for capturing a tissue sample. The biopsy needle is in a loaded state when sent to the target site and then fired forward for sample intake. For example, in prostate cancer the biopsy sample covers a volume 1.5 cm from the needle tip [11].

Mishra et al. [12] discloses a real time bioimpedance measuring biopsy needle 200. It measures the impedance between the inner needle tip 201 and outer needle tip 202.

International application published under publication number WO 2011/016034 describes a surgical tool for use in a tissue removal procedure from a subject. The surgical tool has proximal and distal regions and at least one sensor for sensing one or more predetermined conditions located at a distal region of the surgical tool. The surgical tool further comprises a substantially flat signal transmission structure electrically connected with the at least one sensor and extending between the location at the distal region and the proximal region. The signal transmission structure is configured for providing impedance controlled signal transmission between the at least one sensor and the proximal region.

OBJECTIVE OF THE INVENTION

Albeit the Mishra biopsy needle 200 provides insight on the needle location, the electrode configuration generates the sensitivity distribution around the needle, backwards from the needle tip. The inventors have found out that the problem with this is that because the biopsy instrument 200 fires the needle forward, the actual biopsy is taken much further than where the main portion of the measured impedance originates.

Biopsy device for biopsy sampling is also presented in publication WO 2009/142918 A2.

The first objective of the present invention is to improve biopsy sampling accuracy of sampling performed by using a biopsy needle or a biopsy device as described and claimed herein.

According to a further aspect of the invention, the second objective of the present invention is to improve manufacturing of biopsy needles or biopsy devices that have improved biopsy sampling accuracy.

The first objective can be achieved by the biopsy needle for biopsy sampling as claimed and disclosed herein as well as by biopsy device for biopsy sampling in accordance with the disclosure and claims herein. The second objective can be fulfilled with any one of the methods according to the method claims set forth and described herein.

The dependent claims describe advantageous embodiments of the arrangement and of the methods.

ADVANTAGES OF THE INVENTION

In accordance with the present invention, there is provided a biopsy needle for biopsy sampling, comprising a cannula with a distal end, an inner needle that has a sharpened distal end, and at least one biopsy cavity that is located at a distance from the sharpened distal end. The cannula and the inner needle are configured so that the inner needle is accommodated inside the cannula and the inner needle and the cannula are movable with regard to each other.

The inner needle further comprises at least two measuring electrodes, working as a pair, for measuring a bioimpedance spectrum. There are several methods of providing pairs of measuring electrodes. The pairs of measuring electrodes define a measuring volume that is essentially localized around the distal end of the inner needle. Of each pair of measuring electrodes, at least one is a wire electrode. The inner needle further comprises a shell that may serve, in one embodiment, as a measuring electrode and a polymer filled core that functions as an electrical insulation between the shell serving as a measuring electrode and the wire electrode. In this manner, it is possible to add a number of wire electrodes inside the shell, e.g. before or during injection moulding.

Advantageously, the biopsy needle for biopsy sampling can provide an enhanced biopsy needle to have more accurate tissue samples, biopsies, because the biopsy needle for biopsy sampling enables sampling from the same volume that is measured with the cocked biopsy needle in an essentially localized fashion.

Preferably, at least two of the measuring electrodes reach the sharpened distal end of the inner needle; such as by extending to the surface of the sharpened distal end.

Alternatively or in addition to this, the inner needle may have a beveled needle facet and the measuring volume may be focused on the beveled needle facet.

Advantageously, the biopsy needle may have a measurement sensitivity that is defined as the ratio between the volume in front of the sharpened distal end to the measuring volume, or alternatively as measurement sensitivity arising from a biopsy sampling volume in front of the sharpened distal end to the measuring volume. The measurement sensitivity may be more than 50%, preferably more than 90%, even more preferably more than 95%, and most preferably over 98%.

The volume of the biopsy cavity and the measuring volume may be mutually so selected that a majority (such as at least 50%, preferably at least 90%, more preferably at least 95%, and most preferably at least over 98%) of the measuring volume will be fitted into the biopsy cavity.

Advantageously, the position of the measuring electrodes, the length and location of the biopsy cavity along the inner needle may be selected in such a manner that the firing by a firing part of a biopsy device moves the biopsy cavity in such a manner that the tissue most sensitively measured at the time of firing will be captured into the biopsy cavity.

If the ratio between measurement sensitivity arising from a biopsy sampling volume in front of the sharpened distal end to the measuring volume is more than 90%, preferably more than 95% and most preferably over 98%, the tissue type that will be contained in the biopsy sample may be determined more accurately.

The length and location of the biopsy cavity along the inner needle have been selected in such a manner that the firing by a firing part of a biopsy device moves the biopsy cavity into the measuring volume so that the measuring volume will be essentially covered by the biopsy cavity, most preferably so that the distance between the biopsy cavity and the measuring volume essentially covers the range of 10.5-11.5 mm, 16.5-17.5 mm, or 21.5-22.5 mm. It is possible to enable spatially accurate measurement that represents better the same volume as the tissue sample has been taken.

With the inner needle which further comprises a conduit leading to the biopsy cavity enabling vacuuming of the biopsy cavity, it is possible to improve biopsy sampling by attracting the tissue sample stronger to the bottom of biopsy cavity by suction.

When at least one electrode is a wire electrode and is placed eccentrically within the inner needle in such way that the wire electrode runs essentially straight from the proximal end of the inner needle to the distal end while passing the biopsy cavity under the bottom of the biopsy cavity, it is possible to measure the impedance only on the very tip of the needle. Advantageously even 98% of the total sensitivity can be located in front of the needle facet.

When the wire electrode is located at an edge of the inner needle, it is possible to measure the impedance only on the very tip of the sharpened needle.

When the wire electrode is curved within the inner needle at the distal end of the biopsy needle, it is possible to position the wire electrode to the desired location on the facet.

When the biopsy needle comprises two halves that have been placed against each other, comprising recesses that form at least one passage for the wire electrode, it is possible to have even very complex recesses in the inner needle.

When the inner needle has a solid volume that serves as one measuring electrode, it is possible to manufacture a biopsy needle with high young's modulus.

When the wire electrode is located in a longitudinal recess that is located in the solid volume, most preferably on the opposite side of the biopsy cavity, it is possible to measure the impedance only on the very tip of the sharpened needle.

When the wire electrode is insulated from the solid volume by a dielectric (in particular, by a layer of electrical insulation), it is possible to use the solid volume as a measuring electrode and to measure the impedance only on the very tip of the sharpened needle.

The biopsy device for biopsy sampling comprises i) a biopsy needle according to the present invention, ii) a biopsy tool handle, to which the biopsy needle has been attached or is attachable, and iii) a firing part, which is configured to fire or move the inner needle outwards from the cannula and to make the cannula to follow the inner needle in such a way that at least the inner needle moves a punch length forward and the cannula follows it by moving from behind of the biopsy cavity past the biopsy cavity in order to capture a tissue sample. It is possible to improve biopsy sampling accuracy with the biopsy device.

When the biopsy needle is configured to pick a tissue sample from a volume which spatially covers the measuring volume, it is possible to enable a spatially accurate measurement that represents better the same volume as the tissue sample has been taken.

With the manufacturing method comprising the biopsy needle constructed of two halves that are joined, it is possible to manufacture even very complex recesses to the inner needle for example by extruding. The recess may easily be made to have a desired shape.

With the method wherein each of the halves comprises a recess, in such a manner that the joined biopsy needle comprises a passage for a wire electrode, it is possible to avoid breaking the wire electrode when the halves are pressed together.

With the method wherein the passage is curved at the distal end so that the wire electrode will become curved when installed, it is possible to manufacture a curved wire electrode and to avoid breaking the wire electrode when the halves are pressed together.

With the method wherein the radius of the curving of the passage is selected by the intended use of the biopsy needle, it is possible to manufacture the biopsy needle for certain defined purposes.

With the manufacturing method comprising the wire electrode installed inside the biopsy needle before or during the filling of the shell, for example before or during the injection moulding, it is possible to speed up the installation of the wire electrode and/or to avoid cutting, drilling and milling of the filling for accommodating the wire electrode.

With the manufacturing method comprising the core and shell glued to each other, it is possible to join the core and the shell faster.

With the manufacturing method comprising the core and shell joined together by using thermal expansion or thermal shrinking of the materials, it is possible to reduce the number of the materials used in the manufacturing.

LIST OF DRAWINGS

The invention is gone through in more detail in the following by way of the exemplary embodiments shown in the attached drawings in FIG. 2 to 13.

In the drawings:

FIG. 12 is a longitudinal cross-section of a third embodiment of the biopsy needle; and FIG. 13 is a locally enlarged cross-section of the third embodiment of the biopsy needle shown in FIG. 12.

Similar parts are marked with identical reference numbers in all FIGS.

DETAILED DESCRIPTION

Figure 2:
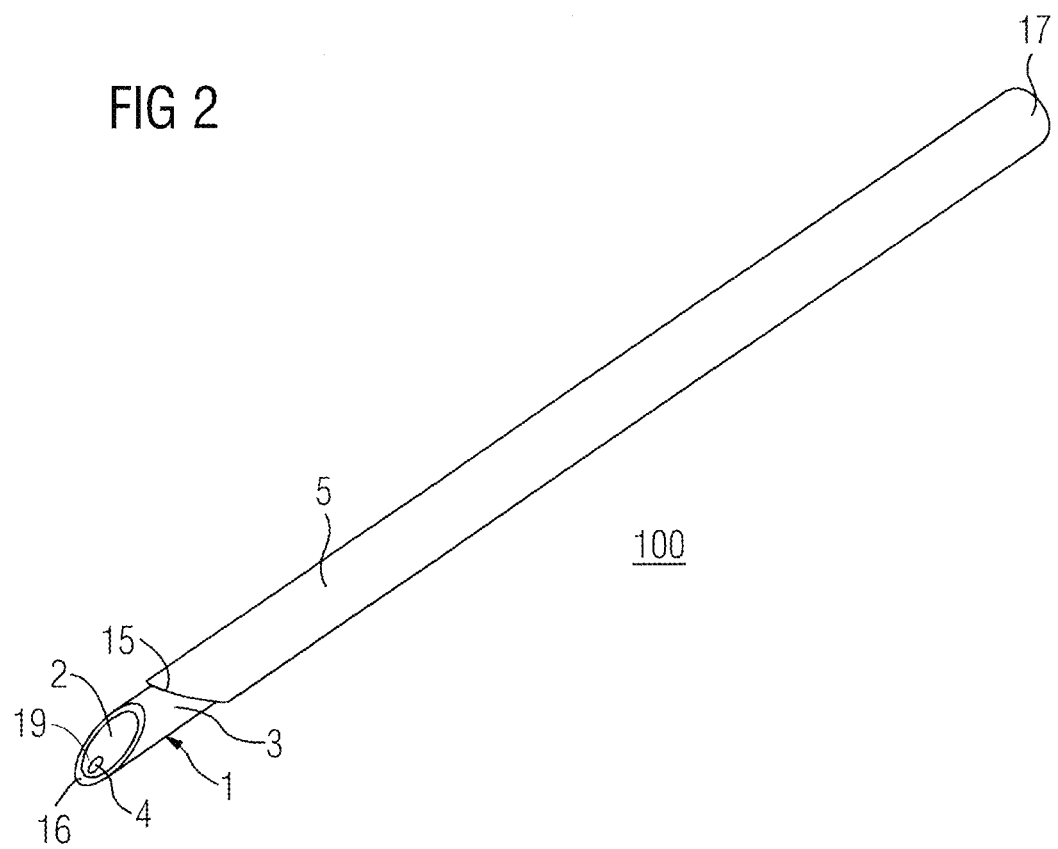
FIG. 2 is a perspective view of a biopsy needle in accordance with the preferred embodiment of the present invention wherein the measurement is performed from the very tip of the foremost needle.
Figure 7:
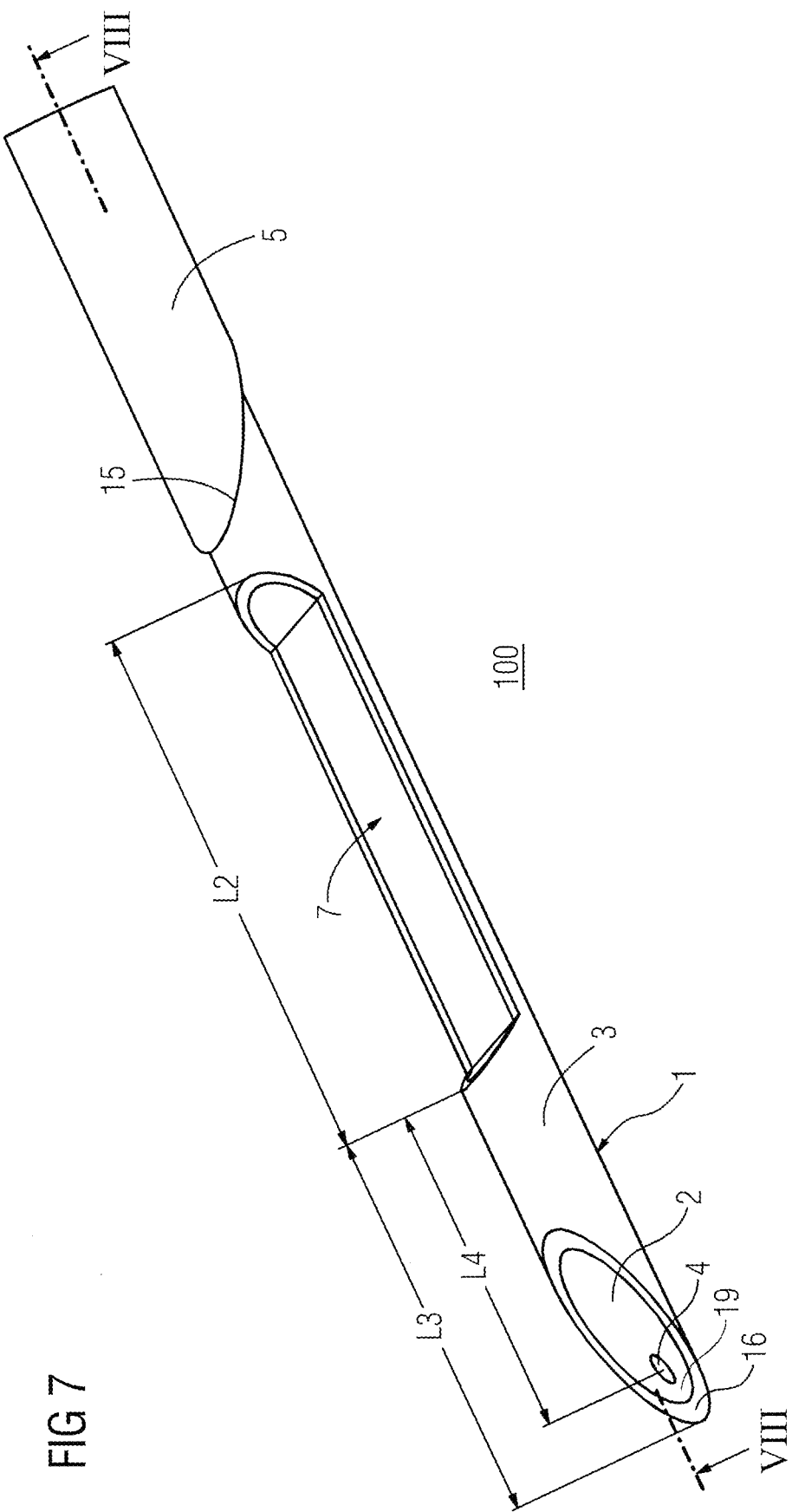
FIG. 7 is a perspective view of the biopsy needle of FIG. 2 when the inner needle has been fired forward, but before the shell has advanced from behind the biopsy cavity past the biopsy cavity.
Figure 8:
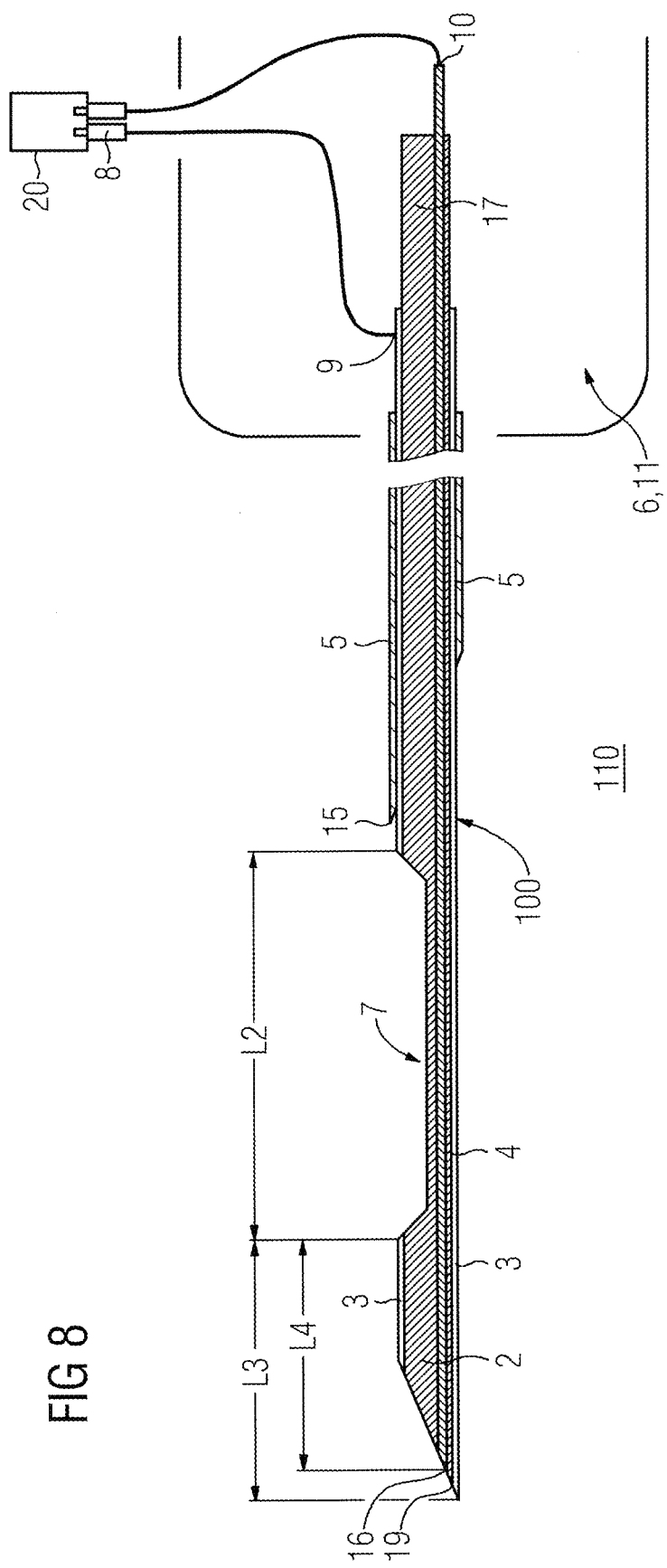
FIG. 8 is a longitudinal cross-section of a biopsy device with a biopsy needle of FIG. 7 with a biopsy tool handle.

Referring to FIGS. 2, 7 and 8, a biopsy needle 100 for biopsy sampling comprises a cannula 5 with a distal end 15, an inner needle 1 that has a sharpened distal end 16, and at least one biopsy cavity 7 that is located at distance L3 from the sharpened distal end 16 of the inner needle 1.

The cannula 5 and the inner needle 1 are configured so that the inner needle 1 is accommodated inside the cannula 5 and the inner needle 1 and the cannula 5 are movable with regard to each other. The inner needle 1 comprises a shell 3 that is a measuring electrode and a polymer filled core 2 that insulates the shell 3 galvanically from the wire electrode 4 located in the core 2. Core 2 can also comprise or consist of metal, polymer alloy/epoxy or/and composite material polymer and glass fiber, for example. The core 2 should preferably in all cases have a high young's modulus to manufacture a rigid inner needle 1. The cannula 5 is preferably made of steel or other material that can be enabling manufacture of the sharpened cutting edge to the distal end 15.

Shell 3 and wire electrode 4 function as two measuring electrodes for measuring a bioimpedance spectra. Both are located before the biopsy cavity 7 as seen from the distal end 16, while at least one 4 of the measuring electrode is located along the distance L4 and/or essentially only in the distal end 16 of the inner needle 1 preferably in such a manner that measuring electrodes define measuring volume that is localized around the distal end 16 of the inner needle 1, namely, focused on the beveled needle facet 19.

Figure 3:
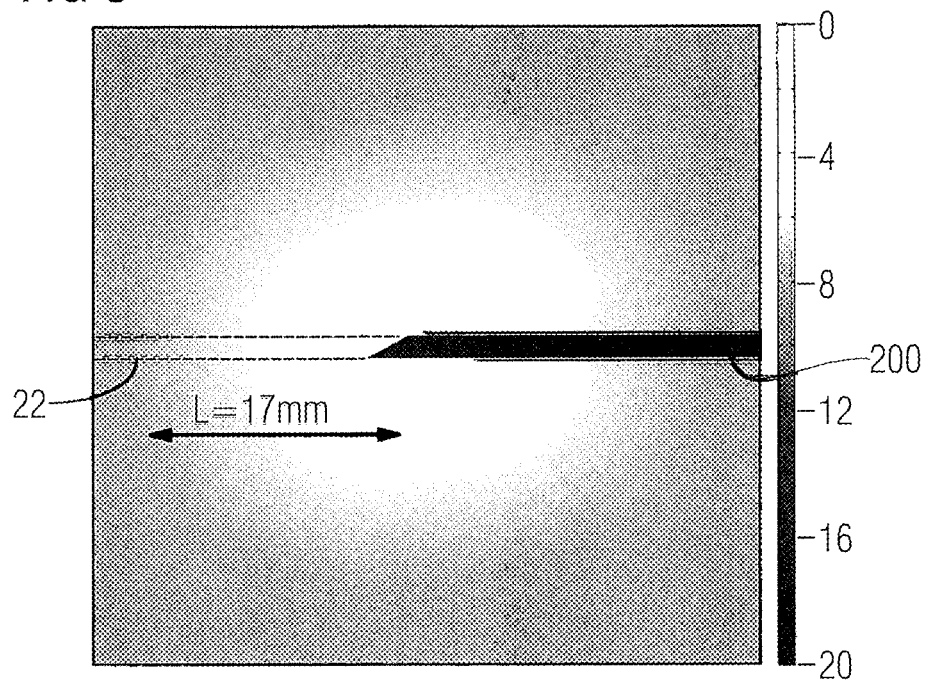
FIG. 3 is a cross-section of the 3D simulated sensitivity distribution for biopsy needle known from Mishra et al., in which the impedance is measured between the inner needle tip and outer needle tip.

The measuring volume is localized in front of the inner needle 1 for more than 90% and most preferably for more than 95% or over 98%. This can be seen in FIG. 4, where the region with relative value of sensitivity is between 0 and −6(in $\log_{10}$ scale), between 0 and −5 (in $\log_{10}$ scale), or even between 0 and −4 (in $\log_{10}$ scale). The measuring volume is represented in FIG. 3 and in FIG. 4 as essentially white area.

The length L2 and location of the biopsy cavity 7 along the inner needle 1 are preferably selected in such a manner that the firing by a firing part 11 of a biopsy device 110 moves the biopsy cavity 7 into the measuring volume so that the measuring volume is possible to be essentially covered by the biopsy cavity 7, most preferably so that the distance L4 between the biopsy cavity 7 and the measuring volume essentially covers the range of 10.5-11.5 mm, 16.5-17.5 mm, or 21.5-22.5 mm.

The inner needle 1 can further comprise a conduit 12 leading to the biopsy cavity 7 enabling vacuuming of the biopsy cavity 7.

The wire electrode 4 is preferably placed eccentrically within the inner needle 1, advantageously in such way that the wire electrode 4 runs essentially straight from the proximal end 17 of the inner needle 1 to the distal end 16 while passing the biopsy cavity 7 preferably under the bottom of the biopsy cavity 7. The wire electrode 4 can be located at an edge of the inner needle 1.

FIG. 12 shows an embodiment where the wire electrode 4 can be curved within the inner needle 1 at the distal end 16 of the biopsy needle 100. The inner needle 1 further can comprise a conduit 12 leading to the biopsy cavity 7 enabling vacuuming of the biopsy cavity 7. The biopsy needle 100 can comprise two halves that have been placed against each other, comprising recesses 14 that together form at least one passage 18 for the wire electrode 4.

In the manufacturing method of a biopsy needle 100 or a biopsy device 110, the biopsy needle 100 may be constructed of two halves 21 that are joined. Each of the halves 21 comprises a recess 14, in such a manner that the joined biopsy needle 100 comprises a passage 12 for a wire electrode 4. The passage 18 may be curved at the distal end so that the wire electrode 4 will become curved when installed. The radius of the curving of the passage 12 is selected by the intended use of the biopsy needle.

Figure 9:
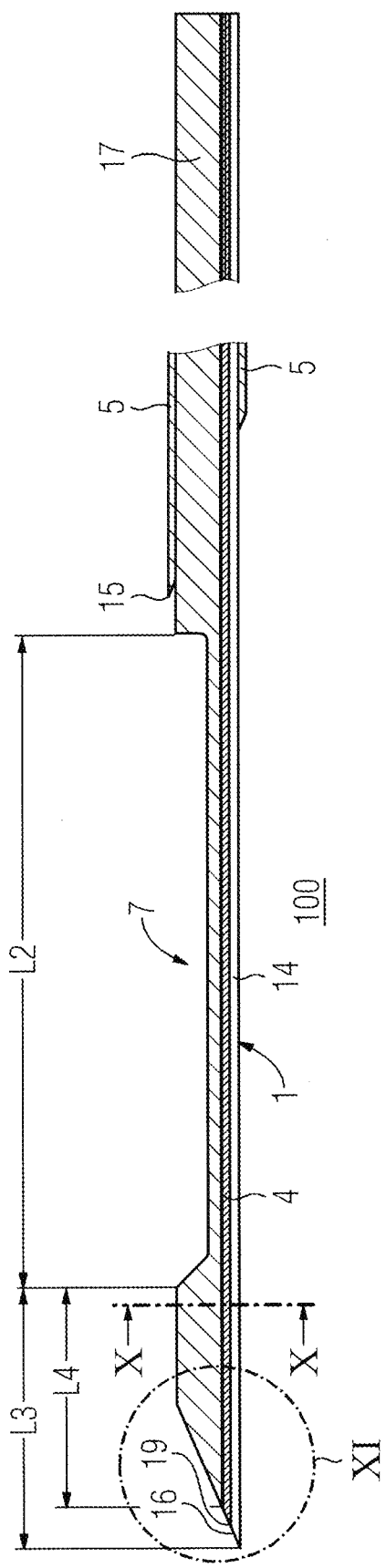
FIG. 9 is a longitudinal cross-section of a second embodiment of the biopsy needle.
Figure 10:
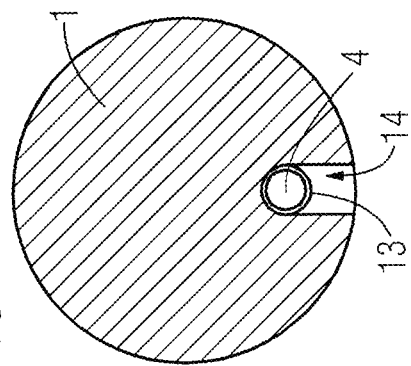
FIG. 10 is a cross-section taken along line X-X of the second embodiment of the biopsy needle shown in FIG. 9.

FIG. 9 shows an embodiment where the inner needle 1 can have a solid volume that is a measuring electrode. The wire electrode 4 can be located in a longitudinal recess 14 that is preferably located in the solid volume, most preferably on the opposite side of the biopsy cavity 7. The wire electrode 4 is insulated from the solid volume by a dielectric 13, FIG. 10.

As shown in FIG. 8, a biopsy device 110 for biopsy sampling comprises i) a biopsy needle 100, ii) a biopsy tool handle 6, to which the biopsy needle 100 has been attached or is attachable, and iii) a firing part 11, which is configured to fire the inner needle 1 outwards from the cannula 5 and to make the cannula 5 to follow the inner needle 1 in such a way that at least the inner needle 1 moves a punch length L forward and the cannula 5 follows it by moving from behind of the biopsy cavity 7 past the biopsy cavity 7 in order to capture a tissue sample, and after the cannula 5 has passed over the biopsy cavity 7. As explained above, the biopsy needle 100 is configured to pick a tissue sample preferably from the volume which spatially covers the measuring volume. The biopsy device 110 further can comprise an electrical connection 8 to a measurement device 20, an electrical coupling to the inner needle 1 and an electrical coupling 10 to the electrode wire 4.

In the manufacturing method of a biopsy needle 100 or a biopsy device 110, wire electrode 4 may installed inside the biopsy needle 100 before or during the filling of the shell 3, for example before or during injection moulding.

In the manufacturing method of a biopsy needle 100 or a biopsy device 110, the core 2 and shell 3 may glued to each other's.

Alternatively, in the manufacturing method of a biopsy needle 100 or a biopsy device 110 the core 2 and shell 3 may be joined together by using thermal expansion of the materials.

I. Materials and Methods

A. Bioimpedance Probe Biopsy Needle

The developed bioimpedance probe (BIP) biopsy needle is 14 G core type biopsy needle 1 although other sizes may also be used. It consists of two nested stainless steel needles: inner needle 1 and cannula 5 as the conventional biopsy needle, but the inner needle 1 is a tube, filled with polymer material and wire electrode 4 (preferably of stainless steel). Polymer material insulates the wire electrode 4 from the shell 3.

Figure 1:
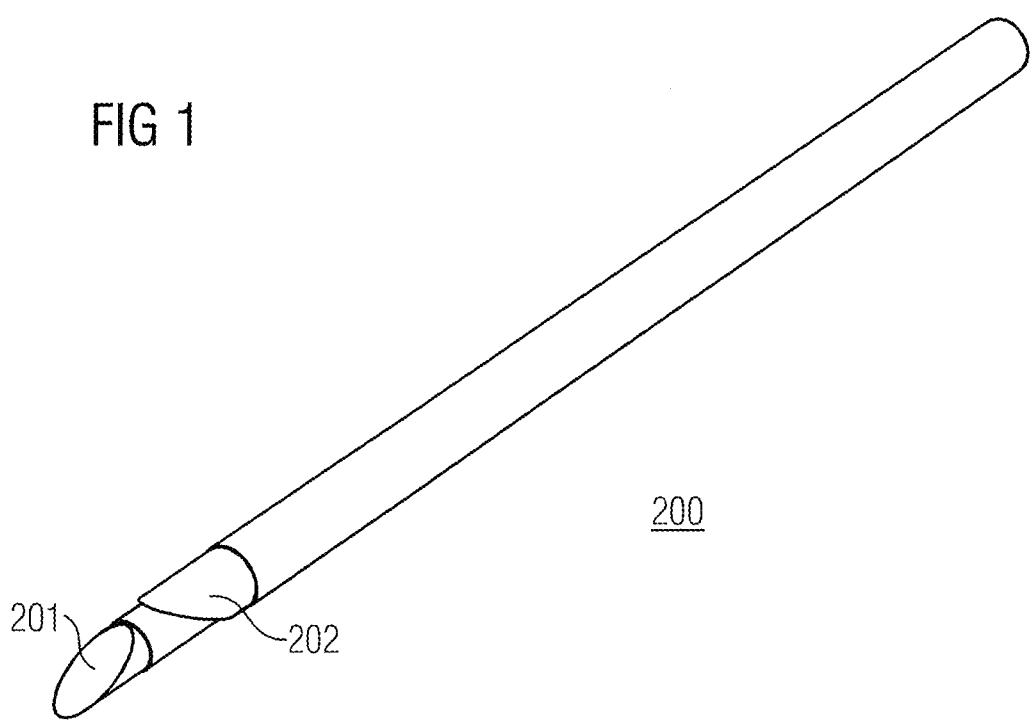
FIG. 1 is a perspective view of a conventional biopsy needle for biopsy sampling as known from Mishra et al., in which the impedance is measured between the inner needle tip and outer needle tip.
Figure 11:
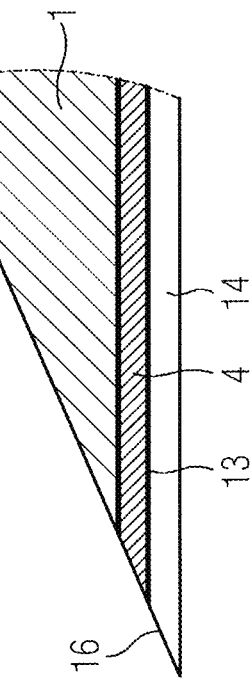
FIG. 11 is a locally enlarged view XI of the second embodiment of the biopsy needle as shown in FIG. 9.

The wire electrode 4 is preferably placed eccentrically to the other edge of the needle cannula 5 (see FIG. 1). As a result, the electrode 4 can continue from the needle handle 6 straight to the tip of the needle 16 by lying under the biopsy cavity 7. By these means, the measurement sensitivity is brought to the very tip of the needle, to distal end 16 (cf. detail XI in FIG. 9 shown in detail in FIG. 11).

Biopsy needle 100 measures bioimpedance spectrum preferably in bipolar fashion and the measurement principle preferably similar as described by Kari et al [4]. The biopsy instrument is connected to measurement device which may be an IEC 60601 compatible bioimpedance analyzer developed by Injeq Oy. The measurement device may provide the impedance and phase angle spectra in real-time from multiple measurement freguencies between 1 kHz and 349 kHz. Sampling frequency of the device can be 200 Hz, for example.

B. Simulation of Sensitivity Distribution

The sensitivity distribution of biopsy needle 200 and biopsy needle 100 were simulated using 3D finite element method. Both biopsy needles 100, 200 are simulated in a size of 18 G. In biopsy needle 100, as explained above the measurement is performed from the tip of the inner needle 1 at distal end 16.

Both biopsy needles 100, 200 were simulated in 50 mm×50 mm×50 mm homogeneous medium so that the needle tip was in the middle of the medium. The boundary conditions were such that charge was not allowed to accumulate to the medium nor to pass the boundaries of the medium.

The measured impedance is defined as $$Z = \int_V \frac{1}{\sigma} S dV, \quad (1)$$

in which σ is conductivity and S sensitivity distribution in the volume V. Using the reciprocity theorem, sensitivity can be calculated as a vector dot product $$S = \vec{J}_{reci} \cdot \vec{J}_{current} \quad (2)$$

In the equation, $\vec{J}_{reci}$ and $\vec{J}_{current}$ are the current density vectors. Since in bipolar configuration the same measurement electrodes act for current feeding and for measurement, the equation reduces to $$S = |\vec{J}_{current}|^2 \quad (3)$$

For analysis, the sensitivity distribution was normalized to the maximal sensitivity in order to obtain comparable graphs of sensitivity distributions of two biopsy needles.

Since the biopsy is taken in front of the needle tip, we calculated the ratio between measurement sensitivity arising from a cylindrical volume in front of the needle tip to the total sensitivity. The cross section of the cylinder is the same as the one of the inner needle 1, 201. The cylinder starts from the facet 19 of the inner needle 1, 201 and ends to the length L where the front end of the biopsy cavity 7 reaches when fired. Thus, the cylinder represents the volume (i.e. biopsy sampling volume 22) where the biopsy is expected to be sampled. The total voltage between the feeding and receiving electrodes corresponds to the total measurement sensitivity. The ratio of sensitivity in the cylinder to the total sensitivity describes how well the measurement represents the biopsy that will be taken and how much medium next to the needle tip affects the measurement.

C. Animal Study

The biopsy needle 100 was tested in vivo with an anesthetized piglet. Muscle C, adipose A, liver B and kidney D tissue were measured with multiple punctures. During the puncture, data was collected from moving biopsy needle 1 which was loaded. Thus, it represents the authentic biopsy procedure. The study was authorized by the ethical committee (ESAVI-6377) of Finland and controlled by experienced veterinarian.

The punctures were performed in visual control in order to ensure that the correct tissue type was reached. The tissue sample was taken only after the data collection in order to prevent unnecessary tissue damage. One puncture lasted about 5 s-10 s and the total amount of data from muscle C and liver B tissue resulted in 1 min and from adipose A and kidney D about in 30 s. The mean and standard deviation was calculated over the time containing all different punctures.

Due to electrode polarization phenomena and measurement error the absolute impedance and phase angle results are not relevant and are comparable only with the results measured with the same measurement setup. More important than the actual values are, however, the differences between tissues. That provides an insight whether the tissue discrimination is possible to perform by using our BIP Biopsy needle 100 and the utilized measurement device.

II. Results And Discussions

A. Sensitivity Distribution

The sensitivity distribution with the Mishra biopsy needle 200 is spherical and located around the biopsy needle 200 (FIG. 3). The values on the scale are relative values of sensitivity field ($\log_{10}$). It measures in front of the needle tip 201, but also next to it and behind the foremost tip.

Figure 4:
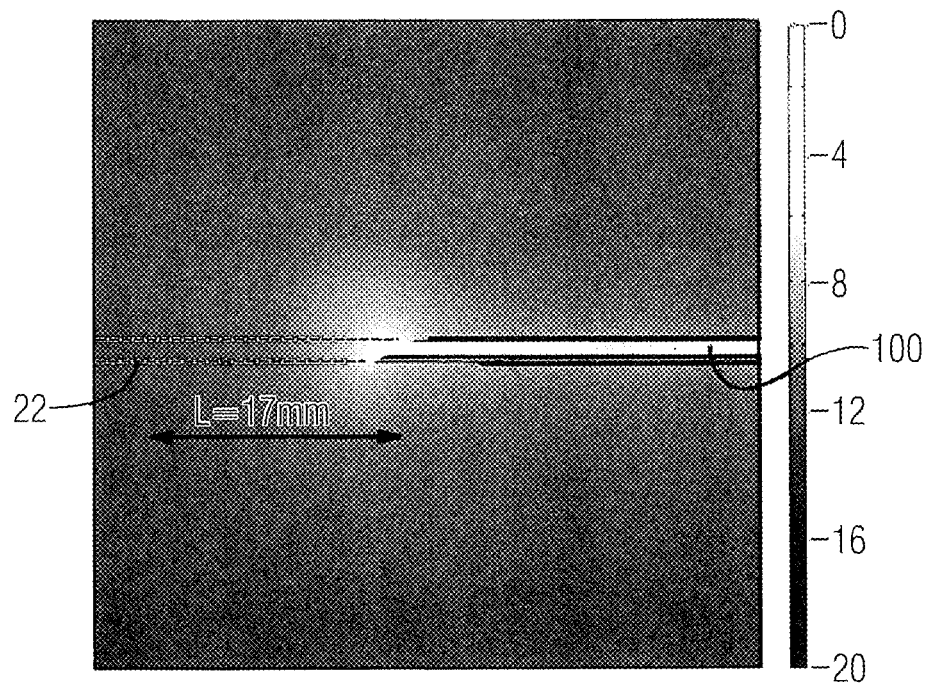
FIG. 4 is a cross-section of the 3D simulated sensitivity distribution for the biopsy needle and the device disclosed in the present specification, in which the measurement is performed from the very tip of the foremost needle.

FIG. 4 represents the sensitivity simulation of the biopsy needle 100. Also in FIG. 4, the values on the scale are relative values of sensitivity field ($\log_{10}$). As can be seen, the distribution is focused on the needle facet 19 to smaller volume than with the other biopsy needle 200 (FIG. 3). In practice, the biopsy needle 100 does not measure anything next to the biopsy needle 100 or behind it.

An advantage of the Mishra biopsy needle 200 may be that it at least in theory might be more robust and it could provide a more steady signal. If the whole volume is homogeneous, it provides representative results. However, heterogeneities next to the needle tip 201 do affect the measurement results and the Mishra biopsy needle 200 is not so sensitive to small targets. Even if biopsy needle 200 would detect the target, the desired sample may get missed since the measurement is performed from a much larger volume than the tissue sample is taken.

Biopsy needle 100, 200 is fired by firing part the needle parts about 2 cm (e.g. 11 mm, 17 mm or 22 mm) in front of the loaded needle. Thus, the biopsy is taken only in front of the needle tip. The measurement result behind or next to the needle tip is irrelevant.

For biopsy needle 100, 98.3% of the total measurement sensitivity is from the volume in front of the needle tip (distal end 16). With the Mishra biopsy needle 200, the corresponding value is only 4.85%. According to the simulation results, only biopsy needle 100 enables spatially accurate measurement that represents better the same volume as the tissue sample will be taken.

B. Spectra of In Vivo Tissues

Figure 5:
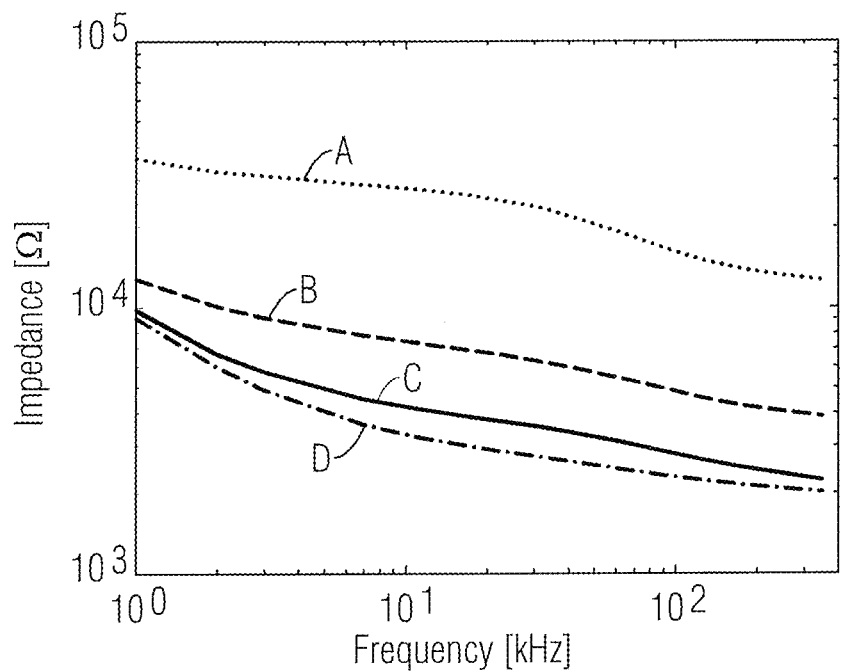
FIG. 5 is a diagram of the mean impedance of in vivo tissues of adipose, liver, muscle and kidney.
Figure 6:
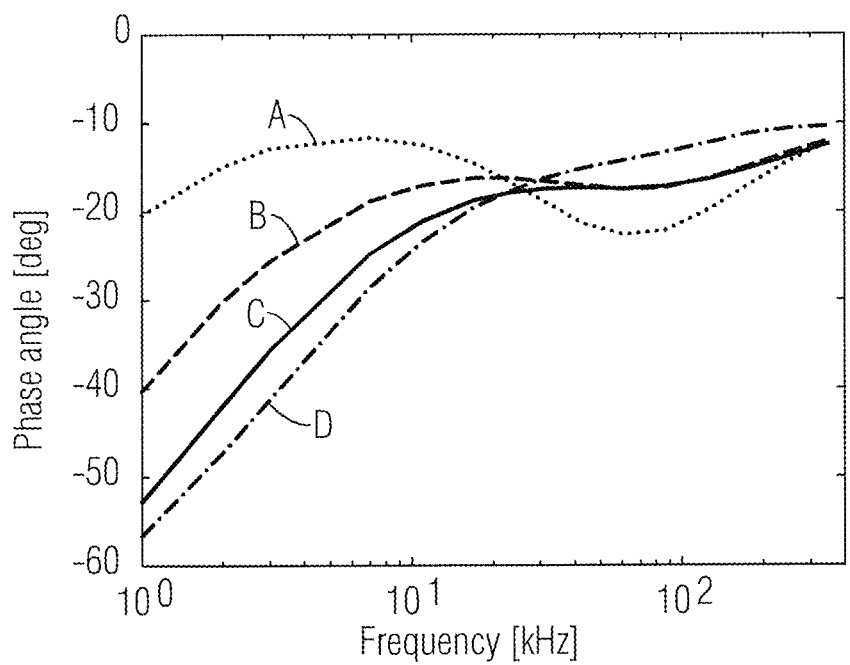
FIG. 6 is a diagram of the phase angle spectra of in vivo tissues of adipose, liver, muscle and kidney.

Impedance spectrum (in Ω) and phase angle spectrum (in degrees) of in vivo tissues are shown in FIG. 5 and 6, respectively. A denotes adipose tissue, B denotes liver tissue, C denotes muscle tissue and D denotes kidney tissue.

The absolute measurement values are not important since they contain measurement error, boundary impedance and other systematic characters related to the measurement setup. The interesting part is the differences of spectra from different tissue types.

In addition to tissue properties, the measured values are dependent on the measurement setup. Boundary conditions and noise affect them. The deviation of the absolute results from the true impedance can be safely ignored, as long as the errors are mostly systematic, i.e. measurement results are well repeatable and the results differ substantially for different tissue types.

Adipose tissue (A) is less conductive than the other tissues, as expected. Kidney tissue (D) is the most conductive material and it has the smallest standard deviation. In phase angle spectra, different tissues show different kind of frequency behavior. Kidney tissue (D) has the strongest frequency dependence and its phase angle changes from −60° to −10° when measurement frequency increases from 1 kHz to 349 kHz.

Phase angle values overlap each other in frequencies 10 kHz-50 kHz and 200 kHz-349 kHz, but in other frequencies, the values are at least one standard deviation away from the others. Over all, the tissues differentiate from each other when using multiple measurement frequencies and the information of impedance and phase angle spectra.

Since the spectra of different tissues differ from each other, it is possible to create classifier for tissue discrimination. Similar mathematical classifier could be used as in Injeq's BIP Needles [4]. Results are promising, and the study should be continued with deeper analysis about differences between benign and cancerous tissues, damaged or healthy tissue in specified medical application. If their electrical properties differ significantly as expected, biopsy needle 100 could provide a tool for targeting the tissue sample more accurately than is possible without the measurement.

III. Conclusions

Representative biopsy is important for diagnosis but challenging to achieve without targeting methods. Bioimpedance can be utilized for identification of the location of the needle tip. Previous design measured impedance around the Mishra biopsy needle 200. With that design heterogeneities next to the needle affect the measurement result and therefore there is a risk of missing the target. Biopsy needle 100 and biopsy device 110 improve the spatial resolution and measure the impedance only on the very tip of the biopsy needle 100.

According to the simulation results with the Mishra biopsy needle 200, only 5% of the measurement sensitivity distribution was in front of the needle tip. With biopsy needle 100, 98% of the total sensitivity lies in front of the needle facet 19.

Animal studies with our BIP Biopsy needle 100 provided promising results: Adipose A, muscle C, liver B and kidney D tissues had different kinds of frequency spectra. According to the preliminary results, the biopsy needle 100 has potential to be developed for biopsy targeting tool. Further study will be performed with cancerous tissues for specific applications.

It is obvious to the skilled person that, along with the technical progress, the basic idea of the invention can be implemented in many ways. The invention and its embodiments are thus not limited to the examples described above but they may vary within the contents of patent claims and their legal equivalents.

REFERENCES

[1] Ratziu, V., Charlotte, F., Heurtier, A., Gombert, S., Giral, P., Bruckert, E., . . . & LIDO Study Group "Sampling variability of liver biopsy in nonalcoholic fatty liver disease." Gastroenterology 128.7 (2005): 1898-1906.

[2] Sonn, G. A., Natarajan, S., Margolis, D. J., MacAiran, M., Lieu, P., Huang, J., . . . & Marks, L. S. "Targeted biopsy in the detection of prostate cancer using an office based magnetic resonance ultrasound fusion device." The Journal of urology 189.1 (2013): 86-92.

[3] Kalvoy, H., Frich, L., Grimnes, S., Martinsen, G., Hoi, P. K., & Stubhaug, A. "Impedance-based tissue discrimination for needle guidance." Physiological measurement 30.2 (2009): 129.

[4] Kari J, Annala K, Annus P, Seppa V-P and Kronstrom K. "A thin needle with bio-impedance measuring probe: tissue recognition performance assessed in in vivo animal study." Available at www.injeq.com, BRC 3.0, 2015, cited in Dec. 5, 2015.

[5] Kimura, S., Morimoto, T., Uyama, T., Monden, Y., Kinouchi, Y., & Iritani, T. "Application of electrical impedance analysis for diagnosis of a pulmonary mass." Chest Journal 105.6 (1994): 1679-1682.

[6] Morimoto, T., Kimura, S., Konishi, Y., Komaki, K. , Uyama, T., Monden, Y. , . . . & Iritani, D. T. "A study of the electrical bio-impedance of tumors." Investigative Surgery 6.1 (1993): 25-32.

[7] Jossinet, J. "The impedivity of freshly excised human breast tissue." Physiological measurement 19.1 (1998): 61.

[8] Halter, R. J., Schned, A., Heaney, J., Hartov, A., & Paulsen, K. D. "Electrical properties of prostatic tissues: I. Single frequency admittivity properties." the Journal of Urology 182.4 (2009): 1600-1607.

[9] Halter, R. J., Schned, A., Heaney, J., Hartov, A., & Paulsen, K. D. "Electrical properties of prostatic tissues: II. Spectral admittivity properties." The Journal of urology 182.4 (2009): 1608-1613.

[10] Inagaki, T., Bhayani, S. B., Allaf, M. E., Ong, A. M., Rha, K. H., Petresior, D., . . . & Kavoussi, L. R. "Tumor capacitance: electrical measurements of renal neoplasia." The Journal of urology 172.2 (2004) : 454-457.

[11] Patel, Amit R., and J. Stephen Jones. "The prostate needle biopsy gun: busting a myth." The Journal of urology 178.2 (2007): 683-685.

[12] Mishra, V., Bouayad, H., Schned, A., Hartov, A., Heaney, J., & Halter, R. J. "A real-time electrical impedance sensing biopsy needle." Biomedical Engineering, IEEE Transactions on 59.12 (2012): 3327-3336.

LIST OF REFERENCE NUMBERS USED

L length
L1 length
L2 length
L3 distance
L4 distance
A adipose
B liver
C muscle
D kidney
1 inner needle
2 core
3 measuring electrode (in shell)
4 wire electrode
5 cannula
6 biopsy tool handle
7 biopsy cavity
8 electrical connection
9 electrical coupling
10 electrical coupling
11 firing part
12 conduit
13 dielectric
14 recess
15 distal end
16 distal end
17 proximal end
18 passage
19 facet
20 measurement device
21 halve
22 biopsy sampling volume
100 biopsy needle
110 biopsy device
200 biopsy instrument
201 inner needle tip
202 outer needle tip Modifications and substitutions by one of ordinary skill in the art are considered to be within the scope of the present invention, which is not to be limited except by the allowed claims and their legal equivalents.

The invention claimed is:

1. A biopsy needle (100) for biopsy sampling, comprising:
a cannula (5) with a distal end (15);
an inner needle (1) that has a sharpened distal end (16); and
at least one biopsy cavity (7) disposed in said inner needle (1) and that is located at a distance (L3) from the sharpened distal end (16) of said inner needle (1); and wherein: the cannula (5) and the inner needle (1) are configured so that the inner needle (1) is accommodated inside the cannula (5) and the inner needle (1) and the cannula (5) are movable with regard to each other; the inner needle (1) further comprising:
at least two measuring electrode pairs (1,4; and 3,4) for measuring a bioimpedance spectrum of tissue into which at least one pair of said at least two measuring electrode pairs (1,4, and 3,4) are disposed, said at least pair one of the at least two measuring electrode pairs defining a measuring volume that is localized around a distal end (16) of the inner needle (1), and wherein at least one of each of the at least two measuring electrode pairs (1,4, and 3,4) is a wire electrode (4); and
a shell (3) that is a measuring electrode for one pair (3,4) of the at least two measuring electrode pairs includes a polymer filled core (2) that functions as an electrical insulation between the shell (3) and the wire electrode (4).

2. The biopsy needle (100) according to claim 1, wherein: each measuring electrode of the at least two measuring electrode pairs (1,4; and 3,4) reach the sharpened distal end (16) of the inner needle (1) by extending to a surface of the sharpened distal end (16).

3. The biopsy needle (100) according to claim 1, wherein: the inner needle (1) has a beveled needle facet (19) and wherein the measuring volume is focused on the beveled needle facet (19).

4. The biopsy needle (100) according to claim 3, wherein: the biopsy needle (100) has a measurement sensitivity that is defined as a ratio between a volume in front of the sharpened distal end (16) of the inner needle (1) to the measuring volume, or alternatively, as the measurement sensitivity arising from a biopsy sampling volume (22) in front of the sharpened distal end (16) to the measuring volume.

5. The biopsy needle (100) according to claim 4, wherein: the measurement sensitivity is greater than 50%.

6. The biopsy needle (100) according to claim 1, wherein: the volume of the biopsy cavity (7) and the measuring volume are selected that at least 50% of the measuring volume is fitted into the biopsy cavity (7).

7. The biopsy needle (100) according to claim 1, wherein: a position of at least one pair of measuring electrodes of the at least two measuring electrode pairs (1,4; and 3,4) and a length (L2) and location of the biopsy cavity (7) along the inner needle (1) have been selected in such a manner that a firing by a firing part (11) of a biopsy device (110) moves the biopsy cavity (7) in such a manner that a tissue sample whose bioimpedance spectrum has been measured at the time of firing is catched into the biopsy cavity (7).

8. The biopsy needle (100) according to claim 1, wherein: a length (L2) and location of the biopsy cavity (7) along the inner needle (1) have been selected in such a manner that a firing by a firing part (11) of a biopsy device (110) moves the biopsy cavity (7) into a measuring volume so that the measuring volume will be essentially covered by the biopsy cavity (7), most preferably so that a distance (L4) between the biopsy cavity (7) and the measuring volume covers a range of 2 cm, 10.5-11.5 mm, 16.5-17.5 mm, or 21.5-22.5 mm.

9. The biopsy needle (100) according to claim 1, wherein: the inner needle (1) further comprises a conduit (12) leading to the biopsy cavity (7) enabling vacuuming of the biopsy cavity (7).

10. The biopsy needle (100) according to claim 1, wherein: the wire electrode (4) is placed eccentrically within the inner needle (1) in such way that the wire electrode (4) runs straight from a proximal end (17) of the inner needle (1) to the distal end (16) while passing the biopsy cavity (7) under a bottom of the biopsy cavity (7).

11. The biopsy needle (100) according to claim 10, wherein: the wire electrode (4) is located at an edge of the inner needle (1).

12. The biopsy needle (100) according to claim 10, wherein: the wire electrode (4) is curved within the inner needle (1) at the distal end (16) of the biopsy needle (100).

13. The biopsy needle (100) according to claim 10, wherein: the biopsy needle (100) comprises two halves that have been placed against each other, comprising recesses (14) that form at least one passage (18) for the wire electrode (4).

14. The biopsy needle (100) in accordance with claim 1, wherein: the inner needle (1) has a solid volume that is a measuring electrode.

15. The biopsy needle (100) according to claim 14, wherein: the wire electrode (4) is located in a longitudinal recess (14) that is located in a solid volume on the opposite side of the biopsy cavity (7).

16. The biopsy needle (100) in accordance with claim 15, wherein: the wire electrode (4) is insulated from the solid volume by a dielectric (13).

17. The biopsy needle (100) in accordance with claim 1, wherein: said biopsy needle (100) is configured for use in a biopsy device (110) for biopsy sampling, said biopsy device further including:
   i) a biopsy tool handle (6), to which the biopsy needle (100) has been attached or is attachable; and
   ii) a firing part (11), which is configured to fire the inner needle (1) outwards from the cannula (5) and to make the cannula (5) to follow the inner needle (1) in such a way that at least the inner needle (1) moves a punch length (L) forward and the cannula (5) follows the inner needle (1) by moving from behind of the biopsy cavity (7) past the biopsy cavity (7) in order to capture a tissue sample.

18. The biopsy device (110) according to claim 17, wherein: the biopsy needle (100) is configured to pick a tissue sample from a volume of tissue which spatially covers the measuring volume.

19. A method of manufacturing the biopsy needle (100) according to claim 1, wherein: the biopsy needle (100) is constructed of two halves that are joined.

20. The method according to claim 19, wherein: each of the halves comprises a recess (14), in such a manner that the joined biopsy needle (100) comprises a passage (12) for a wire electrode (4).

21. The method according to claim 20, wherein: the passage (18) is curved at the distal end so that the wire electrode (4) will become curved when installed.

22. The method according to claim 21, wherein: the radius of the curving of the passage (12) is selected by the intended use of the biopsy needle (100).

23. A method of manufacturing a biopsy needle (100) according to claim 1, wherein: the wire electrode (4) is installed inside the biopsy needle (100) before or during the filling of the shell (3).

24. A method of manufacturing a biopsy needle (100) according to claim 1, wherein: the core (2) and shell (3) are glued to each other.

25. A method of manufacturing a biopsy needle (100) according to claim 1, wherein: the core (2) and shell (3) are joined together by using thermal expansion of the materials.

* * * * *